United States Patent [19]
Visinoni et al.

[11] Patent Number: 6,042,874
[45] Date of Patent: Mar. 28, 2000

[54] PROCESS FOR PROCESSING ORGANIC SPECIMENS

[75] Inventors: Francesco Visinoni, Bergamo, Italy; Werner Lautenschläger, Leutkirch, Germany

[73] Assignee: Milestone S.r.l., Bergamo, Italy

[21] Appl. No.: 09/051,031

[22] PCT Filed: Aug. 1, 1997

[86] PCT No.: PCT/EP97/04207

§ 371 Date: Nov. 23, 1998

§ 102(e) Date: Nov. 23, 1998

[87] PCT Pub. No.: WO98/05938

PCT Pub. Date: Feb. 12, 1998

[30] Foreign Application Priority Data

Aug. 2, 1996 [EP] European Pat. Off. .............. 96112571

[51] Int. Cl.[7] .............................. A01N 1/00; B05D 1/34
[52] U.S. Cl. .............................. 427/2.11; 427/4; 427/296
[58] Field of Search .......................... 427/4, 2, 11, 336, 427/595, 296, 553

[56] References Cited

U.S. PATENT DOCUMENTS

| | | | |
|---|---|---|---|
| 3,889,014 | 6/1975 | Kinney et al. | 427/4 |
| 4,839,194 | 6/1989 | Malluche et al. | 427/4 |
| 4,891,239 | 1/1990 | Dudley | 427/4 |
| 4,911,915 | 3/1990 | Fredenburgh | 424/3 |
| 5,089,288 | 2/1992 | Berger | 427/4 |
| 5,318,795 | 6/1994 | Stokes et al. | 427/4 |
| 5,431,952 | 7/1995 | Ocello | 427/4 |

OTHER PUBLICATIONS

The Two–Step Vacuum–Microwave Method for Histoprocessing Mathilde E. Boon; C.H. Wals–Paap; F.A. Visinoni; L.P. Kok European Journal of Morphology, vol. 33, No. 4, 1995 Microwave Newsletter p. 349–358 XP 000614291 (no month).

*Primary Examiner*—Diana Dudash
*Attorney, Agent, or Firm*—Lacasse & Associates; Randy W. Lacasse; Wesley L. Strickland

[57] ABSTRACT

This invention relates to the processing of organic tissues to prepare them for further investigation such as by light microscopy, electron microscopy, microwave staining, immunostaining, decalcification, hybridisation etc.

The present invention discloses a process for processing organic tissue, which comprises the steps of fixing an organic sample to be processed, dehydrating and clearing the sample and subsequently infiltrating and embedding the sample in a supporting medium to prepare it for further examination wherein the steps of dehydrating and clearing are carried out simultaneously by applying a mixture of a dehydration agent and an essentially lipophilic agent simultaneously to the sample.

49 Claims, 2 Drawing Sheets

PROCESS FOR PROCESSING ORGANIC SPECIMENS

The present invention relates to the processing of organic tissues to prepare them for further investigation. More specifically the present invention relates to a process for processing organic tissue via a combination of microwave, vacuum and pressure treatment comprising the steps of fixing an organic sample, dehydrating and clearing the sample, and subsequently infiltrating and embedding the sample in a supporting medium to prepare it for basic Haematoxylin and Eosinstans and further techniques such as microwave staining, immunostaining, decalcification, hybridisation etc., for subsequent examination by light and electron microscopy.

Biopsies for diagnostic pathology and for anatomy pathology are presently prepared according to a conventional method, which is based on the following essential steps:
1. The tissue to be examined is treated with formaline or a saline solution to stop the —process of decay and to stabilise the tissue so as to protect it against physical and chemical rigours of the processing.
2. In the second step the sample is dehydrated, i.e. some or all of the free water contained in the specimen ist removed therefrom. During this procedure various cellular components are dissolved by the dehydrating fluids, such as lipids, which are extracted, and water soluble proteins, which are dissolved in aqueous alcohols.
3. The third step includes the treatment of the tissue with another solvent, the so-called clearing agent. Clearing is the transition step between dehydration and infiltration with the supporting medium. Since many dehydrants are immiscible with said subsequently applied supporting medium, a solvent is used which is miscible both with the dehydrant and the embedding medium to facilitate the transition between dehydration and infiltration steps.
4. The last step in the processing of organic specimens involves infiltrating the tissue cavities and cells by the supporting substance and finally embedding the tissue in the medium which will provide sufficient external support during the ensuing processing.

These procedures show, however, a variety of disadvantages, such as a long processing time of the specimens which may amount up to 50 hours per sample. Furthermore, a huge amount of the dehydrating agent and the clearing agent has to be employed. In a normal procedure the specimens are treated several times with the dehydrating agent, e.g. ethanol in rising concentrations (up to 100% ethanol), and subsequently several times with the clearing agent in order to get rid of the dehydrating agent. Since large amounts of solvents have to be used, said solvents even being of high purity, the costs of such procedures are rather high.

A histoprocessing procedure with a shortened processing time is for example known, from the article "The Two-Step Vacuum-Microwave Method for Histoprocessing" by M. E. Boon et al., European Journal of Morphology, Vol. 33, No. 4, 1995, pages 349–358. The histoprocessing method of organic tissues disclosed therein includes the steps of fixing the tissue, dehydrating the sample, clearing the sample and embededing the sample in paraffin, whereby the dehydrating and the clearing of the sample are carried out simultaneously in 100%—isopropanol in a vacuum chamber and heated by microwaves. Isopropanol is used in this step because it is both a weak dehydrator and a claring agent. In this step the temperature is controlled at 55° C. and the pressure at 0,04 MPa (400 mbar) so that the tissue can withstand the hazards of the treatment without adverse affects.

On the other hand it proved to be difficult in practice to properly process organic tissue samples having a substantial amount of lipids contained therein (fatty tissue). In this case, the free water to be removed is retained in the tissue to a large extent making the use of excessive amounts of dehydrating agent necessary, which eventually results in an inferior quality of the specimens. This fact was considered to be due to fat cells embodied in the respective specimens preventing a free migration of water out of the tissue.

An alternative technique has been developed to reduce the time delay between receipt of the biopsy material in the laboratory and the availability of the tissue for further examination, and to rapidly obtain thin slides of the respective material. The biopsies are frozen in liquid nitrogen and then cut at lower temperature in a cryostat microtome. However, the specimens processed according to this method show a rather poor quality.

Hence there was a need in the art for an improved process for processing organic samples which obviates the above problems.

According to an aspect of the present invention there is provided a process for processing organic tissue which comprises the steps of
(i) fixing an organic sample to be processed,
(ii) dehydrating the sample with dehydration agent,
(iii) clearing the sample with an essentially lipophilic agent, and
(iv) impregnating the sample,
wherein said steps (ii) and (iii) are carried out simultaneously by applying a mixture of the dehydration agent and the essentially lipophilic agent simultaneously to the sample.

Other aspects and advantages of the present invention will be readily apparent to the skilled person when reading the present specification together with the claims taking into account the accompanying drawings.

The first step in the processing of organic tissue is the fixatikon of the respective specimen. In the process of the present invention there is no particular limitation as to the fixation method utilized. Hence strategies commonly employed to ensure fixation may be used. Methods suitable in the process of the present invention included microwave irradiation of biopsy specimens in normal saline, continuing fixation on the tissue processor with one or more changes of the routine fixative, preferably at elevated temperatures of 40 to 60° C., secondary fixation in formol sublimate on the tissue processor or in alcoholic fixative which will complete fixation while initiating dehydration, fixing in buffered phenol-formaldehyde pH 7.0 and pH 5.5 sequence at 40° C., etc.

In the second step according to the present process the specimens are treated with a combination of a dehydrating agent and an essentially lipohilic agent, i.e. a clearing agent.

As the dehydrating agent to be used in the present process there may be mentioned compounds which are essentially of hydrophilic nature. Examples for said compounds comprise lower alcohols, preferably alcohols containing 1 to 8 carbon atoms, lower ethers, preferably ethers containing 1 to 8 carbon atoms, ketones, preferably acetone, phenols, anilines, tetrahydrofuran, 2,2-dimethoxypropan, 2,2 diethoxypropan and creosote. Since any of these compounds reveal specific advantages for a given purpose or for a specific tissue specimen, the person skilled in the art will select the appropriate one for the respective task, or a mixture thereof.

Especially preferred dehydrating agents include alcohols, such as methanol, ethanol, propanol, isopropanol, n-butanol and t-butanol, or mixtures of these. Isopropanol or a mixture of isopropanol and ethanol is most preferred.

As the clearing agent to be used together with the dehydration agent in the present process there may be mentioned compounds, which are essentially of amphiphilic or lipophilic nature, which agents should preferably be miscible with the respective dehydrating agent utilized. Examples for said clearing agents include aliphatic hydrocarbons, which may be straight or branched, and which may be substituted with halides, such as chlorine, bromine or iodine. Also aromatic hydrocarbons may be used, which may be substitued by a moiety, comprising from 1 to 4 carbon atoms or which may be substituted by halides, such as chlorine, bromine or iodine. Also alkanes, esters and terpenes have been found to be suitable clearing agents in the present process.

Specific examples include toluene, xylene, benzene, petroleum, paraffin, carbon disulphide, chloroform, carbon tetrachloride, trichlorethane, n-butylacetate, amylacetate, methyl benzoate, methyl salicylate, cedarwood oil, clove oil, inhibisol (inhibisol is the tradename of a cleaning fluid consisting of 1,1,1-trichlorethane with inhibitors designed to reduce its toxicity), limonene, terpineol and mixtures thereof. Preferred agents are aliphatic and aromatic hydrocarbons with said aliphatic hydrocarbon having from 6 to 12 carbon atoms, preferably 6 to 10, most preferably n-hexane, n-heptane and n-octane, being more preferred. Also a preferred clearing agent is n-olein.

Based on his general knowledge and the teaching of the present invention the person skilled in the art will select the appropriate combination of the dehydration agent and the clearing agent for a given purpose. Thus, when treating e.g. fatty tissue a combination of a dehydration agent and a clearing agent will be chosen which allows a rapid extraction of lipids.

Preferred combinations of a dehydration agent and a clearing agent are alcohols combined with alithatic and/or aromatic hydrocarbons. A combination of alcohols, having 1 to 4 carbon atoms, together with aliphatic and/or aromatic hydrocarbons is more preferred with the combination of isopropanol with one or more of petroleum, ether, n-hexane, n-heptane, n-octane, n-olein, chloroform and/or acetone being most preferred. Instead of using isopropanol alone a combination of ethanol and isopropanol is more preferably employed.

The amount of the dehydrating agent and the clearing agent in the solvent combination utilized may vary depending on the tissue to be treated and the properties inherent to the respective agents. A ratio of dehydrating agent: clearing agent of 20–80:80–20% by volume are within the scope of the present invention. A preferred ration is 50:50 more preferred 60:40. In case of the preferred mixture of ethanol and isopropanol and an alkane all constituents are preferably included in equal amounts by volume. Unexpectedly it has been shown that the use of isopropanol in the dehydration/clearing agent results in the sample to be easily cut for later investigation.

The dehydration/clearing step is preferably carried out at a pressure of from atmospheric pressure to 1 MPa (10 bar), preferably at slightly elevated pressure, i.e. 0.11 to 0.5 MPa, and up to 1 MPa. Treatment under pressure allows for the sample to be treated at higher temperatures, namely at a temperature of from room temperature up to 90° C., preferably 70 to 90° C., more preferably 70 to 85° C., most preferred at a temperature of from 80 to 85° C. without causing the combination of dehydration/clearing agent to evaporate and disrupting the tissue structure. The pressure may be effected by simply heating the sample in a closed container with the evaporating liquids building up a slight pressure. It is, however, preferred to build up the pressure by introducing a gas in the container, such as an inert gas, preferably nitrogen gas or carbon dioxide.

Surprisingly it has been found that the above conditions of pressure and temperature also result in a smoother defatting of samples without causing a denaturation of proteins and cell structures in the sample. Thus the morphology of the cell is fully maintained. Further this step is preferably carried out in a microwave device since it has been shown that heating of the sample may smoothly be effected by microwave treatment.

Before carrying out the impregnation step the sample is dried, said process being primarily effected by means of moderate heat, i.e. heating the sample at a temperature from 30 to 60° C., preferably 60° C. In order to promote the removal of residula water and solvent the drying process should be carried out under reduced pressure, preferably at a pressure in the range of from 0.01 to 0.05 MPa, more preferably at 0.01 MPa. Methodes currently employed also involve a quick rinse of the moist tissue cassettes with alcohol, preferably ethanol, no less than 80% concentration.

In the impregnation step (iv) of the present process the sample is infiltrated by and embedded in a medium the properties of which should generally approach those of the tissues to be examined with regard to density, elasticity, plasticity, viscosity and adhesion and should be harmless to the embedded material. Generally the infiltration medium and the embedding medium are equal, but they may be different as well. Suitable materials to be used as infiltration and/or as embedding medium include compounds selected from the group consisting of agar, gelatine, polyvinylalcohol, polyetherglycols, polyethylene glycol monostearate, diethylene glycol distearate, ester wax, polyester wax, nitrocellulose, paraffin wax or a mixture thereof. Additives may be added to the waxes or blends of waxes, such additives being e.g. Piccolyte 115, which is a thermoplastic terpene resin added at the rate of 5–10% to the infiltrating wax, plastic polymers, such as polyethylene wax or dimethylsuloxide (DMSO).

When applying the supporting media to the sample, vacuum should preferably be applied to remove air entrapped in the tissue and to remove residual solvents used in the preceding combined dehydration and clearing step. Thus the impregnation step is preferably conducted under vacuum, starting with a moderate vacuum of from about 0.05 to 0.02 MPa, preferably 0.03 to 0.02 MPa, in order to carefully degas the molten paraffin applied to the sample. In a next step the vacuum is then lowered, preferably to about 0.01 MPa or even 0.005 MPa.

Alternatively the impregnation step may also be carried out by alternately applying a moderate pressure, such as from 0.1 to 0.5 MPa, preferably 0.11 to 0.3 MPa for a time period of about 5 minutes or less, preferably 3 or 4 minutes, more preferred about 2 minutes, and a moderate vacuum for about the same time period. The reduced pressure to be applied ranges of from 0.01 to 0.08 MPa, preferably from 0.01 to 0.05 MPa, more preferred from 0.02 to 0.03 MPa.

According to the present process it became possible to process a variety of tissues including difficult tissues, such as tissues which are largely composed of keratin, dense collagen, closely packed smooth muscle fibres, colloid areas of haemorrhage, thrombi or yolk (hard dense tissues), or mummified tissues or yolk rich tissues and also fatty tissues. In addition it could be shown that the processing time for the specimens could be reduced enormously to about 30 minutes for processing needle biopsies and about 60 to 120 minutes for standard type tissue specimens.

Surprisingly it has been shown that the properties of the respective dehydrating agents and clearing agents are not altered when being combined, thus allowing a simple and efficient dehydration and clearing at the same time. In case of fatty tissues it has furthermore been shown that dehydration may easily be accomplished since the clearing agent also serves for extracting lipid substances, resulting in a smooth removal of the water without deterioration of the structure of the tissue to be treated.

In a preferred embodiment the present process is carried out in a microwave heating device. Microwave treatment has been shown to accelerate the action of cross-linking fixatives and also allows the removal of the dehydrating agent and the clearing agent to proceed more smoothly.

According to another aspect of the present invention there is provided an apparatus for carrying out the above process which comprises (i) a microwave heating device comprising a sealable processing chamber arranged therein,
(ii) a container arranged in said processing chamber for loading the samples,
(iii) a means for applying vacuum to said processing chamber,
(iv) a means for applying pressure to said processing chamber, and
(v) a line for applying vacuum or pressure to said processing chamber, wherein the processing chamber comprises a plate and an automatically liftable dome, wherein said liftable dome encloses the container arranged in said processing chamber, and wherein the line for applying vacuum or pressure to said processing chamber extends through said dome.

In a preferred embodiment one single vacuum/pressure pump unit may be used for applying pressure and vacuum to the processing chamber and for the up and down movement of the dome. Further, the processing chamber may be rotatable by 360° for ensuring a uniform microwave radiation of the samples in the microwave heating device.

Other means for executing said apparatus and preferred embodiments thereof are illustrated in the copending PCT application WO95/19560, the contents of which is fully incorporated herein by way of reference.

With reference to the drawings, the present invention will be further illustrated in the following by way of example, wherein.

The histoprocessing procedure is preferably carried out in a microwave heating device with a microwave generator including a magnetron as a main component thereof for generating microwaves which are by means of a wave guide coupled into the interior of the microwave heating device.

The microwave heating device comprises an access opening and incorporates a rotating glass processing chamber 1, 2 which accomodates up to sixty tissue cassettes contained in a microwave-transparent rack preferably made of PTFE (polytetrafluorethylene), arranged as two concentric circles inside a glass container 3.

The processing chamber 1, 2 consists of a rotatable carousel 2 on the bottom of the microwave heating device and a dome 1 which can be raised and lowered pneumatically so that the glass container 3 can be introduced through the access opening in the microwave heating device into the processing chamber. The processing chamber 1, 2 is connected via connecting means with a vacuum/pressure pump unit, and it comprises a sealing arrangement to close the processing chamber in a vacuum-tight or pressure-tight manner, respectively. Preferably, the vacuum/pressure pump unit causes also the raising and lowering of the dome 1.

The microwave heating device further comprises a temperature sensor, e.g. an IR temperature sensor combined with an IR window in the sidewall of the glass dome, for monitoring the temperature of the chemical solution within the container 3. Alternatively, a fiber optic sensor may be used which is located in the central column of the dome 1 and which is connected to the dome 1 to be raised and lowered together with the dome.

The gas evacuated from the processing chamber 1, 2 is preferably passed through a charcoal filter. An automatic solvent detector may be included in the present apparatus to signal the exhaustion of the charcoal.

The microwave heating device as well as the vacuum/pressure pump unit and the temperature sensor are connected by means of connecting means with and controlled through an interactive touch screen computer and dedicated software which ensures consistency and simplicity of operation. A menu of processing schedules can be activated by touch screen icons with preset parameters for microwave power, time, temperature, vacuum and pressure, all continously monitored and regulated by the computer software. The histoprocessing procedure is simply started by activating the relevant icon on the touch screen computer, and the completion of a selected procedure is indicated by an audible alarm. The system also provides protection of stored programs witch access by means of a key card, ensuring only authorized access of modification or creation of customized processing schedules.

In the following, the histoprocessing procedure of tissues will be exemplarily explained.

Multiple tissue blocks were prepared from a wide range of formalin-fixed surgical specimens, representing malignant and benign tissues, including breast, stomach, uterus and spleen. Three size formats were prepared, representing tissue blocks routinely encountered in surgical pathology laboratories:

1. Needle and endoscopic biopsies—measuring up to 20 mm in length and up to 2.5 mm in diameter
2. Intermediate size—measuring up to 15×10×2.5 mm
3. Large size—measuring up to 25×20×4 mm Up to sixty tissue sections in universal plastic cassettes may be placed in a microwave-transparent plastic rack preferably on the basis of PTFE, followed by a rinse in absolute ethanol to remove coating formalin and water. Next, the rack is placed into the circular glass dish 3 containing a solvent mixture of absolute ethanol, isopropanol and an alkane in a ratio of 1:1:1, a so-called "JFC solution" which is a proprietary name of Milestone/MLS Sorisole, Italy. A PTFE based cover (not shown) is placed on the container 3.

Then the dome 1 of the processing chamber is lifted pneumatically and the container 3 is introduced in the microwave heating device under the glass dome, with the appropriate processing schedule selected. The processing schedule chosen was determined by the largest piece of tissue in the batch being processed. The entire process consisted of three main steps with each controlled by its own preset program, as shown in the FIGS. 1 to 3.

Figure 1:
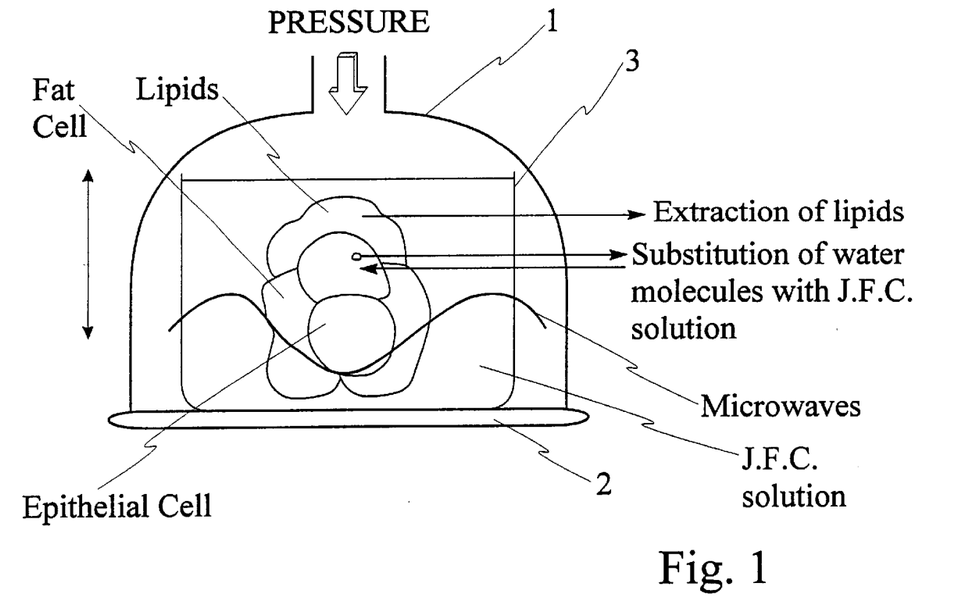
FIG. 1 is a schematic drawing showing the dehydrating and clearing step of a sample.

In the first step shown in FIG. 1, i.e. the dehydration and clearing of the tissues, the JFC solution extracts lipids from fatty tissues releasing the cells, so that under the influence of the microwave the temperature of the water in the cells increases, thereby reducing its viscosity and resulting in a migration of the water towards the external periphery of the cell from where it moves into the solvent solution. This happens in a temperature range which is physiological and not damaging to the tissues.

This step is carried out under pressure of approximately 0.2 MPa to eliminate vaporization of reagents with low boiling point, keeping the concentration constant. As for this reason the temperature can be higher than with known histoprocessing procedures, i.e. up to 80° C.

The dehydration and clearing time of step 1 was for the needle and endoscopic biopsies up to 18 minutes, for intermediate size up to 65 minutes and for large size up to 90 minutes.

At the end of the above first step the dome 1 is automatically raised, the container 3 is taken out from the processing chamber and the microwave heating device and the rack with the cassettes is placed into an empty glass dish 3, this time without a PTFE cover. The container 3 is repositioned under the glass dome 1 in the microwave heating device and a drying program is started by the computer.

Figure 2:
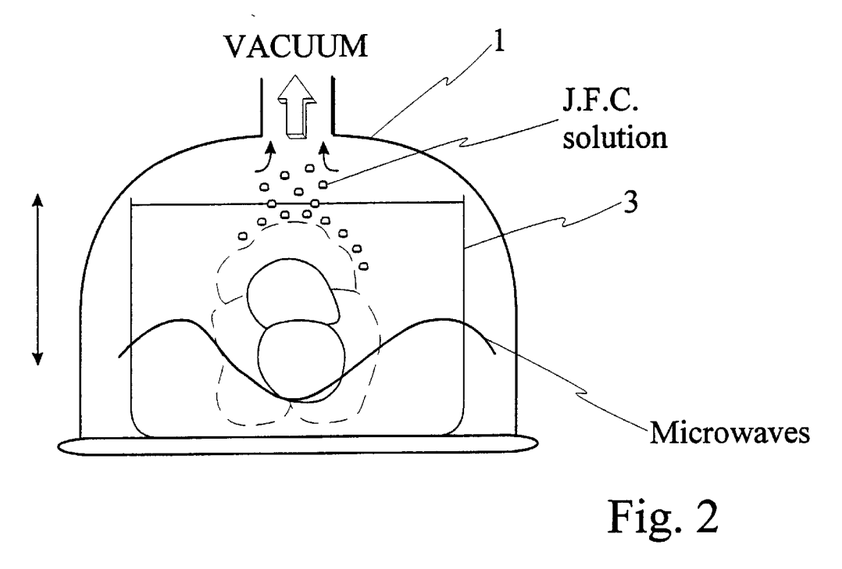
FIG. 2 is a schematic drawing showing the drying step of a sample.

In the second step of drying the tissues shown in FIG. 2, the tissues are prepared for the final wax impregnation, i.e. the remaining JFC solution in the tissues must be removed. This step is carried out under high vacuum of approximately 0.01 MPa and a temperature of about 60° C. The vacuum lowers the boiling and vaporization point temperatures of the JFC reagent and produces complete tissue dehydration and the evaporation of the JFC reagent.

The drying time of step 2 was for the needle and endoscopic biopsies up to 3 minutes and for intermediate and large size up to 5 minutes.

At the end of the above drying step the dome 1 is lifted automatically and the container 3 is taken out from the processing chamber and the microwave heating device. The rack with the plastic cassettes is transferred to a preheated container 3 containing histology grade molten wax of about 65° C. as well as heating elements of WEFLON at the bottom of the container 3 itself. The addition of the heating elements is required to avoid solidification of paraffin which does not absorb microwaves. A WEFLON cover (not shown) is placed on the glass container 3 which is again placed in the microwave heating device under the glass dome 1.

Figure 3:
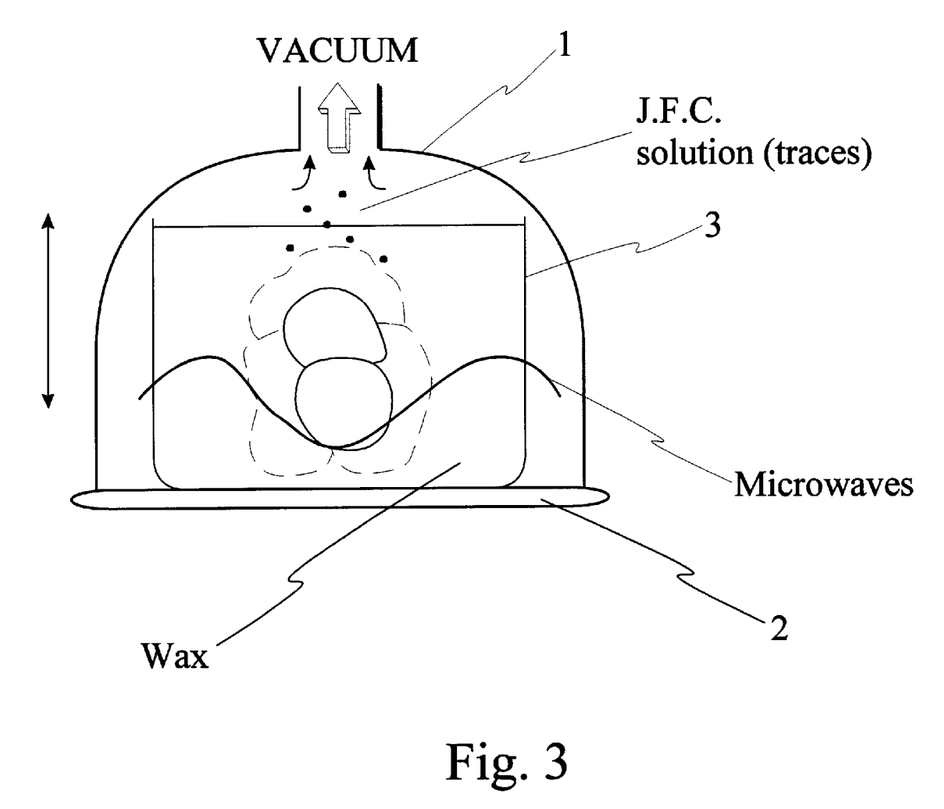
FIG. 3 is a schematic drawing showing the impregnating step of a sample.

In the third step of wax impregnation shown in FIG. 3 any residual traces of JFC solution within the tissues are removed by substitution with molten wax under vacuum of approximately 0.01 MPa. The temperature is set at about 65° C.

The impregnation time of step 3 was for the needle and endoscopic biopsies up to 9 minutes, for intermediate size up to 20 minutes and for large size up to 25 minutes.

On completion of step 3 the dome 1 is lifted automatically and the container 3 is taken out from the processing chamber and the microwave heating device. The tissues within the cassettes are now ready for the conventional embedding, cutting and staining procedures to obtain slides.

The total processing time to paraffin for the specimens were: needle and endoscopic biopsies 30 minutes, intermediate size 90 minutes and large size 120 minutes.

We claim:
1. A process for processing tissue comprising the steps of
  (i) fixing an organic sample to be processed,
  (ii) dehydrating the sample with a dehydration agent,
  (iii) clearing the sample with an essentially lipohilic agent, and
  (iv) impregnating the sample,
    wherein said steps (ii) and (iii) are carried out simultaneously by applying a mixture of said dehydration agent and said essentially lipophilic agent simultaneously to the sample.

2. The process according to claim 1, wherein said sample comprises organic tissue.

3. The process according to claim 2, wherein said organic tissue is from a group comprising blood, nerve tissue and organ tissue.

4. The process according to claim 1, wherein the process further comprises between said steps (ii/iii) and (iv) a step (v) of drying the sample at reduced pressure.

5. The process according to claim 2, wherein the process further comprises between said steps (ii/iii) and (iv) a step (v) of drying the sample at reduced pressure.

6. The process according to claim 2, wherein the dehydration agent is selected from the group consisting of $C_{1-8}$-alcohols, $C_{1-8}$-ethers, ketones and phenols and anilines, tetrahydrofuran, 2,2-dimethoxypropane and 2,2-diethoxypropane and creosote or a mixture thereof.

7. The process according to claim 2, wherein the alcohol is selected from the group consisting of methanol, ethanol, propanol, isopropanol, n-butanol and t-butanol or a mixture thereof.

8. The process according to claim 2, wherein the ether is selected from the group consisting of glycolethers, 2-ethoxyethanol, dioxane and polyethylene glycol or a mixture thereof.

9. The process according to claim 2, wherein the ketone is acetone.

10. The process according to claim 2, wherein the essentially lipophilic agent is selected from the group consisting of aliphatic, aromatic and chlorinated hydrocarbons, alkanes, esters and terpenes or a mixture thereof.

11. The process according to claim 2, wherein the essentially lipophilic agent is selected from the group consisting of n-olein toluene, xylene, benzene, petroleum, paraffin, carbon disulfide, chloroform, carbon tetrachloride, trichloro, n-butylacetate, amylacetate, methyl benzoate, methyl salicylate, cedarwood oil, clove oil, inhibisol, limonene and terpineol or a mixture thereof.

12. The process according to claim 2, wherein the dehydration agent comprises ethanol and isopropanol.

13. The process according to claim 2, wherein the dehydration agent comprises ethanol and isopropanol and the essentially lipophilic agent comprises an alkane.

14. The process according to claim 12, wherein the ethanol, the isopropanol and the essentially lipophilic agent are used in equal amounts.

15. The process according to claim 1, wherein the impregnation step (iv) comprises embedding the sample in a medium selected from the group consisting of agar, gelatine, polyvinylalcohol, polyetherglycols, polyethylene glycol monostearate, diethylene glycol distearate, ester wax, polyester wax, nitrocellulose, paraffin wax or a mixture thereof.

16. The process according to claim 2, wherein the impregnation step (iv) comprises embedding the sample in a medium selected from the group consisting of agar, gelatine, polyvinylalcohol, polyetherglycols, polyethylene glycol monostearate, diethylene glycol distearate, ester wax, polyester wax, nitrocellulose, paraffin wax or a mixture thereof.

17. The process according to claim 1, wherein said steps (ii) and (iii) are carried out under pressure in the range of from 0.11 to 1.0 MPa.

18. The process according to claim 2, wherein said steps (ii) and (iii) are carried out under pressure in the range of from 0.11 to 1.0 MPa.

19. The process according to claim 1, wherein said steps (ii) and (iii) are carried out at a temperature in the range of from 70 to 90° C.

20. The process according to claim 2, wherein said steps (ii) and (iii) are carried out at a temperature in the range of from 70 to 90° C.

21. The process according to claim 17, wherein said steps (ii) and (iii) are carried out at a temperature in the range of from 70 to 90° C.

22. The process according to claim 18, wherein said steps (ii) and (iii) are carried out at a temperature in the range of from 70 to 90° C.

23. The process according to claim 4, wherein said step (v) is carried out at a pressure in the range of from 0.01 to 0.05 MPa.

24. The process according to claim 23, wherein said step (v) is carried out at a temperature in the range of from 30 to 60° C.

25. The process according to claim 4, wherein said step (v) is carried out at a temperature in the range of from 30 to 60° C.

26. The process according to claim 1, wherein the process is carried out in a microwave heating device.

27. The process according to claim 2, wherein the process is carried out in a microwave heating device.

28. The process according to claim 17, wherein the process is carried out in a microwave heating device.

29. The process according to claim 18 wherein the process is carried out in a microwave heating device.

30. The process according to claim 19, wherein the process is carried out in a microwave heating device.

31. The process according to claim 20, wherein the process is carried out in a microwave heating device.

32. The process according to claim 21, wherein the process is carried out in a microwave heating device.

33. The process according to claim 22, wherein the process is carried out in a microwave heating device.

34. The process according to claim 23, wherein the process is carried out in a microwave heating device.

35. The process according to claim 24, wherein the process is carried out in a microwave heating device.

36. The process according to claim 25, wherein the process is carried out in a microwave heating device.

37. The process according to claim 1, wherein said step (iv) is carried out under alternant pressure and vacuum conditions.

38. The process according to claim 4, wherein said step (iv) is carried out under alternant pressure and vacuum conditions.

39. The process according to claim 26, wherein said step (iv) is carried out under alternant pressure and vacuum conditions.

40. The process according to claim 27, wherein said step (iv) is carried out under alternant pressure and vacuum conditions.

41. The process according to claim 28, wherein said step (iv) is carried out under alternant pressure and vacuum conditions.

42. The process according to claim 29, wherein said step (iv) is carried out under alternant pressure and vacuum conditions.

43. The process according to claim 30, wherein said step (iv) is carried out under alternant pressure and vacuum conditions.

44. The process according to claim 31, wherein said step (iv) is carried out under alternant pressure and vacuum conditions.

45. The process according to claim 32, wherein said step (iv) is carried out under alternant pressure and vacuum conditions.

46. The process according to claim 33, wherein said step (iv) is carried out under alternant pressure and vacuum conditions.

47. The process according to claim 34, wherein said step (iv) is carried out under alternant pressure and vacuum conditions.

48. The process according to claim 35, wherein said step (iv) is carried out under alternant pressure and vacuum conditions.

49. The process according to claim 36, wherein said step (iv) is carried out under alternant pressure and vacuum conditions.

* * * * *

UNITED STATES PATENT AND TRADEMARK OFFICE
CERTIFICATE OF CORRECTION

PATENT NO. : 6,042,874
DATED : March 28, 2000
INVENTOR(S) : Visinoni et al.

It is certified that error appears in the above-identified patent and that said Letters Patent is hereby corrected as shown below:

<u>Column 1,</u>
Line 21, the expression "---process" should be replaced with -- process --;
Line 25, the word "ist" should be replaced with -- is --;
Line 62, the word "embededing" should be replaced with -- embedding --;
Line 66, the word "claring" should be replaced with -- clearing --;

<u>Column 2,</u>
Line 39, the word "fixatikon" should be replace with -- fixation --;
Line 61, the expression "2,2-dimethoxypropan, 2,2 diethoxypropan" should be replaced with -- 2,2-diethoxypropan, 2.2-diethoxypropane --;

<u>Column 3,</u>
Line 37, the word "alithatic" should be replaced with -- aliphatic --;
Line 51, the word "ration" should be replaced with -- ratio --;

<u>Column 4,</u>
Line 18, the word "residuala" shoulc be replaced with -- residual --;
Line 41, the word "dimethylsuloxide" should be replace with -- dimethylsulfoxide --;
Line 54, the expression "0.1 to 0.5 Mpa" should be replaced with -- 0.11 to 0.5 Mpa --;

<u>Column 6,</u>
Line 33, the word "witch" should be replace with -- with --;

UNITED STATES PATENT AND TRADEMARK OFFICE
CERTIFICATE OF CORRECTION

PATENT NO.   : 6,042,874
DATED        : March 28, 2000
INVENTOR(S)  : Visinoni et al.

It is certified that error appears in the above-identified patent and that said Letters Patent is hereby corrected as shown below:

Claim 11,
The phrase "selected from the group consisting of n-olein toluene, xylene, benzene, petroleum, paraffin, carbon disulfide, chloroform, carbon tetrachloride, trichloro, n-butylacetate" should read -- selected from the group consistin of n-olein, tolune, xylene, benzene, petroleum, paraffin, carbon disulfice, chloroform, carbon tetrachloride, trichloroethane, n-butylactate --.

Signed and Sealed this

Twenty-eighth Day of August, 2001

*Attest:*

NICHOLAS P. GODICI
*Attesting Officer*     *Acting Director of the United States Patent and Trademark Office*

UNITED STATES PATENT AND TRADEMARK OFFICE
CERTIFICATE OF CORRECTION

PATENT NO. : 6,042,874
DATED : March 28, 2000
INVENTOR(S) : Visinoni et al.

It is certified that error appears in the above-identified patent and that said Letters Patent is hereby corrected as shown below:

Column 1,
Line 21, the expression "—process" should be replaced with -- process --;
Line 25, the word "ist" should be replaced with -- is --;
Line 62, the word "embededing" should be replaced with -- embedding --;
Line 66, the word "claring" should be replaced with -- clearing --;

Column 2,
Line 39, the word "fixatikon" should be replaced with -- fixation --;
Line 61, the expression "2,2-dimethoxypropan, 2,2 diethoxypropan" should be replaced with 2,2-dimethoxypropane, 2,2-diethoxypropane --;

Column 3,
Line 37, the word "alithatic" should be replaced with -- aliphatic --;
Line 51, the word "ration" should be replaced with -- ratio --;

Column 4,
Line 18, the word "residuala" should be replaced with -- residual --;
Line 41, the word "dimethylsuloxide" should be replaced with -- dimethylsulfoxide --;
Line 54, the expression "0.1 to 0.5 MPa" should be replaced with -- 0.11 to 0.5 MPa --;

Column 6,
Line 33, the word "witch" should be replaced with -- with --;

UNITED STATES PATENT AND TRADEMARK OFFICE
CERTIFICATE OF CORRECTION

PATENT NO.   : 6,042,874
DATED        : March 28, 2000
INVENTOR(S)  : Visinoni et al.

It is certified that error appears in the above-identified patent and that said Letters Patent is hereby corrected as shown below:

Claim 11,
The phrase "selected from the group consisting on n-olein toluene, xylene, benzene, petroleum, paraffin, carbon disulfide, chloroform, carbon tetrachloride, trichloro, n-butylacetate" should read -- selected from the group consisting of n-olein, tolune, xylene, benzene, petroleum, paraffin, carbon disulfide, chloroform, carbon tetrachloride, trichloroethane, n-butylacetate --.

This certificate supersedes certificate of correction issued August 28, 2001.

Signed and Sealed this

Twenty-second Day of January, 2002

Attest:

Attesting Officer

JAMES E. ROGAN
*Director of the United States Patent and Trademark Office*